United States Patent [19]

Huth et al.

[11] Patent Number: 5,064,854
[45] Date of Patent: Nov. 12, 1991

[54] 3,4-DISUBSTITUTED PHENYL HETEROCYCLES AND THEIR USE

[75] Inventors: Andreas Huth; Ralph Schmiechen; Helmut Wachtel; Herbert H. Schneider, all of Berlin, Fed. Rep. of Germany

[73] Assignee: Schering Aktiengesellschaft, Berlin and Bergkamen, Fed. Rep. of Germany

[21] Appl. No.: 376,489

[22] Filed: Jul. 7, 1989

[30] Foreign Application Priority Data

Jul. 7, 1988 [DE] Fed. Rep. of Germany ....... 3823299

[51] Int. Cl.⁵ ................. A61K 31/40; C07D 207/273; C07D 403/10; C07D 405/10
[52] U.S. Cl. ..................................... 514/424; 548/543
[58] Field of Search ........................ 548/543; 514/424

[56] References Cited

U.S. PATENT DOCUMENTS

| | | | |
|---|---|---|---|
| 4,186,129 | 1/1980 | Huth et al. | 548/186 |
| 4,193,926 | 3/1980 | Schmiechen et al. | 260/326.5 S |
| 4,198,514 | 4/1980 | Imanishi et al. | 548/543 |
| 4,296,029 | 10/1981 | Bushell et al. | 548/543 |

FOREIGN PATENT DOCUMENTS 0247725 12/1987 European Pat. Off. .
PCT/DE85/-
00472 10/1984 World Int. Prop. O. .

Primary Examiner—David B. Springer
Attorney, Agent, or Firm—Millen, White & Zelano

[57] ABSTRACT

Compounds of general Formula I are disclosed (I)

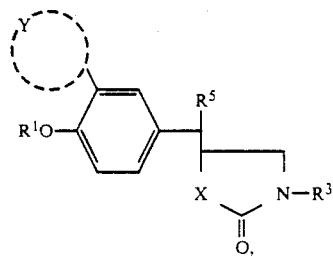

wherein
$R^1$ is $C_{1-4}$-alkyl,
$R^3$ is hydrogen, $C_{1-4}$-alkyl, acyl, aryl,
$R^5$ is hydrogen, $C_{1-4}$-alkyl,
X is oxygen, $CH_2$ or $NR^4$ with $R^4$=hydrogen, $C_{1-4}$-alkyl and
Y is an aromatic or nonaromatic ring system which can optionally contain one to two hetero atoms and can be substituted, and the stereoisomers and their mixtures, as well as their preparation and use as medicinal agents.

19 Claims, No Drawings

3,4-DISUBSTITUTED PHENYL HETEROCYCLES AND THEIR USE

BACKGROUND OF THE INVENTION

The invention relates to novel pyrrolidinone, oxazolidinone and imidazolidinone derivatives, their preparation, and medicinal agents containing same.

U.S. Pat. No. 4,193,926 discloses 4-polyalkoxyphenyl-2-pyrrolidinones, and U.S. Pat. No. 4,186,129 and PCT/DE 85/00472 describe 5-polyalkoxyphenyloxazolidinones, and EP-A-0247725 sets forth 5-(3-polycycloalkoxy-4-alkoxyphenylimidazolidinones. The compounds show neuropsychotropic, inter alia, neuroleptic and antidepressive properties, the imidazolidinones described in EP-A-0247725 being distinguished by a favorable therapeutic index and by reduced emesis.

SUMMARY OF THE INVENTION

The compounds of this invention which surprisingly show a better bioavailability over a prolonged period of time and are distinguished by low gastrointestinal side effects exhibit general Formula I

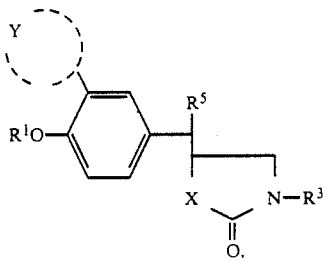

wherein
$R^1$ is $C_{1-4}$-alkyl,
$R^3$ is hydrogen, $C_{1-4}$-alkyl, acyl, $C_{6-12}$-aryl,
$R^5$ is hydrogen, $C_{1-4}$-alkyl,
X is oxygen, $CH_2$ or $NR^4$ ($R^4$=hydrogen, $C_{1-4}$-alkyl) and
Y is an aromatic or nonaromatic ring system which can optionally contain one to two hetero atoms and can be substituted, and the stereoisomers and their mixtures.

Since the compounds of general Formula I possess at least one asymmetrical center, these encompass all possible stereoisomers and mixtures thereof (diastereomers as racemates and enantiomers).

The aromatic or nonaromatic ring system contains 3-12 ring atoms, preferably 5-9 ring atoms and can be monocyclic or bicyclic.

An aromatic ring is understood to mean the aryl as well as hetaryl residue wherein, for example, the following mono- or bicycles can be mentioned: aryl, such as phenyl, biphenylyl, indenyl, naphthyl, and hetaryl of 1-2 hetero atoms, such as sulfur, oxygen and/or nitrogen, such as thienyl, furyl, pyranyl, pyrrolyl, imidazolyl, pyrazolyl, pyridyl, pyrimidinyl, pyridazinyl, oxazolyl, isooxazolyl, thiazolyl, isothiazolyl, benzo[l]thienyl, benzofuryl. Five- to six-membered aromatic ring systems are to be considered preferred; these contain optionally a hetero atom.

A nonaromatic ring system is understood to mean saturated and unsaturated alicyclic and arylalicyclic residues which can be mono- or bicyclic and wherein the rings can be condensed, linked in spiro fashion, or isolated. Examples that can be cited are: cycloalkyl, cycloalkenyl, phenylcycloalkyl, bicycloalkyl, or bicycloalkenyl, such as cyclopropyl, cyclobutyl, cyclopentyl, cyclohexyl, cycloheptyl, cyclooctyl, cyclohexenyl, cyclopentenyl, cycloheptenyl, bicycloheptyl, bicycloheptenyl, indan-2-yl. Suitable hetero atoms for the nonaromatic ring system are 1-2 nitrogen, oxygen and/or sulfur atoms wherein the above-mentioned hetaryls can be partially or entirely hydrogenated. Examples that can be set forth are: pyrrolidinyl, thiazolidinyl, morpholinyl, tetrahydrofuranyl, or tetrahydropyranyl. Preferred nonaromatic ring systems are $C_{3-7}$-cycloalkyl, $C_{3-7}$-cycloalkenyl, norbornane, 1-hydroxy-$C_{3-7}$-cycloalkyl and phenylcycloalkyl, such as indan. If the ring system is substituted, then especially the aromatic is mono- or disubstituted by halogen, $C_{1-4}$-alkyl, $NH_2$ and $OR^2$ wherein $R^2$ is to mean hydrogen, $C_{1-4}$-alkyl, $C_{3-7}$-cycloalkyl and cyclic ethers, such as tetrahydrofuranyl and tetrahydropyranyl.

Halogen can stand for fluorine, chlorine, bromine and iodine.

$C_{1-4}$-alkyl means in each case methyl, ethyl, propyl, isopropyl, butyl, isobutyl, sec-butyl and tert-butyl.

The aryl group $R^3$ is preferably phenyl. Also included for $R^3$ are the aryl groups defined for Y above.

As the acyl residues $R^3$, all organic acids can be utilized that have been cited in U.S. Pat. No. 4,186,129; however, especially preferred are lower alkanoyl groups of up to 4 carbon atoms, such as formyl, acetyl, propionyl, butyryl.

Suitable acyl groups include all residues of physiologically compatible carboxylic acids, e.g., hydrocarbon carboxylic acids. Preferred are alkanoyl groups derived from acids of 1-18 carbon atoms, preferably 2-8 carbon atoms, such as, for example, monobasic acyclic aliphatic carboxylic acids such as formic, acetic, propionic, butyric, isobutyric, a-ethylbutyric, pivalic, valeric, isovaleric, α-ethylvaleric, trimethylacetic, 2-methylbutyric, 3-ethylbutyric, caproic, triethylacetic, enanthic, or caprylic acid; or cyclic acids, preferably cycloaliphatic acids, such as cyclopropylideneacetic, cyclobutylcarboxylic, cyclopentylcarboxylic, cyclopentylacetic, β-cyclopentylpropionic, cyclohexylcarboxylic, or cyclohexylacetic acid. Aroyl groups are also suitable and are derived from carbocyclic aryl, alkaryl or aralkyl acids, such as benzoic acid or 2-, 3-, or 4-methylbenzoic acid. Aryl and aralkyl are as defined above including the substituted versions thereof which include the alkaryl group.

Since the chemical character of the acyl group is not critical for the properties of the compounds of this invention, as long as the acyl group does not have a toxic effect, it is suitable for use in this invention. Thus, also suitable are all such acyl groups derived from aliphatic, araliphatic, and aromatic, acyclic and cyclic (carbo- and hetero-cyclic), unsubstituted and substituted, hydrocarbon and nonhydrocarbon (e.g., having O, S or N atoms), saturated and unsaturated, mono-, di-, and polybasic carboxylic acids of up to 18 carbon atoms, preferably up to 8 carbon atoms.

Suitable acids in this connection include undecylic, dodecanoic, tetradecanoic, hexadecanoic, octadecanoic, palmitic, stearic, and β-cyclohexylpropionic acid; 2,3-, 2,4-, 2,6-, 3,4-, and 3,5-dimethylbenzoic. ethyl benzoic, naphthoic, 3-methyl-α-naphthoic, β-phenylpropionic, diphenylacetic, and α-naphthylacetic acid; carbamic acids, such as carbamic, phenylcarbamic, n- butylcarbamic, dimethylcarbamic, diethylcarbamic, and allophanic acid; and heterocyclic acids, such as β-furylcarboxylic, pyrrolecarboxylic, β-pyrrolidinopropionic, N-methylpyrrolidino-2-carboxylic, 6-hydroxy-indolyl-3-acetic, N-methylmorpholino-2-carboxylic, and pyrrole-2carboxylic acid. As stated, the acyl residues can optionally be mono- or polysubstituted. Suitable substituents include the following: hydroxy, halo, alkyl, alkoxy, carboxy, aralkoxy, acyloxy, sulfonyloxy, amido, sulfato, nitro, mercapto, and cyano wherein aryl, alkyl and acyl are as defined herein.

Thus, suitable acyl residues include those from glycolic, lactic, citric, tartaric, maleic, glyceric, mannonic, gluconic, and salicylic acid; or from amino acids, such as glycine, aminopropionic, diglycolamino triglycolamino, methylglycine, dimethylglycine and diethylglycine acid. Also suitable are the acyl residues of p-amino-salicylic, p-aminobenzoic, ethylmercaptoacetic, benzylmercaptoacetic, chloroaccetic, fluoroacetic, trichloroacetic, trifluoroacetic, thioglycolic, m-nitrobenzoic, 2,3,4-trimethoxybenzoic, phenoxyacetic, and α-naphthyloxyacetic acid; as well as the alkoxylated and aralkoxylated acyl residues of formic acid, such as, for example, carbethoxy and carbobenzyloxy.

Compounds preferred in medicinal agents are those of general Formula I wherein $R^1$ is methyl, $R^3$ is hydrogen and X means $CH_2$ or 0.

The compounds of general Formula I are prepared in accordance with methods known per se, in that, for example, the compounds of general Formula II

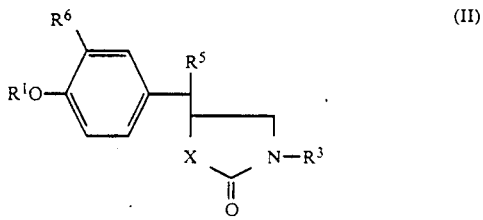

(II)

wherein
$R^1$, $R^3$, $R^5$ and X have the meanings given above and $R^6$ represents a leaving group, (a)

are reacted in the presence of a palladium catalyst with $Y$-boron, $Y$-tin or $Y$-zinc compounds or with cycloalkenes, wherein Y has the meanings given above, or (b)

are converted into a lithium organyl, and the latter is reacted with the corresponding ketone to 1-hydroxycycloalkyl, and optionally the cycloalkene is produced by splitting off water,
and, if desired, subsequently double bonds are hydrogenated and/or NH-groups are alkylated, arylated or acylated and/or ether blocking groups are split off and optionally thereafter etherified and/or the isomers are separated.

Suitable as the leaving groups are halogens, especially bromine and iodine, as well as sulfonates, such as trifluoromethanesulfonate.

Preferred palladium catalysts utilized are organic palladium(II) salts, such as palladium acetate or chloride, optionally in the presence of a ligand, such as triphenylphosphine or tris-ortho-tolylphosphine, or palladium(0) complexes, such as, for example, palladium tetrakistriphenylphosphine in catalytic or larger amounts.

The reaction can be accelerated by bases. Suitable bases are secondary and tertiary amines, such as triethylamine and inorganic bases, such as alkali and alkaline earth hydroxides and carbonates, such as sodium, potassium and lithium hydroxide and thallium hydroxide. The addition of lithium chloride has a positive effect in the reaction of triflates.

The inorganic bases can be dissolved in alcohols or water; the phase transfer can be accelerated by the customary phase transfer catalysts.

Examples of suitable boron, tin and zinc derivatives are organic boronic acids, organic zinc chlorides, and tri-$C_{1-4}$-alkyltin compounds.

The introduction of the ring system takes place in suitable solvents or solvent mixtures at temperatures from room temperature to the boiling temperature of the solution, and is finished after about 1-5 hours.

Suitable solvents are nonpolar solvents, such as toluene, xylene and aprotic polar solvents, such as dimethylformamide, dimethyl sulfoxide, which can, if desired, also be used in mixtures with protic solvents, such as alcohols (methanol, ethanol, and others).

Suitable for conversion into the lithium organyl are, for example, lithium alkyls, such as, in particular, n-butyllithium, tert-butyllithium and phenyllithium. The reaction is performed in aprotic solvents, such as ethers or hydrocarbons, e.g. THF, dioxane, diethyl ether, toluene, hexane, etc., at temperatures of 20° C. to −110° C., preferably 20° C. to −78° C. In order to avoid secondary reactions, the proton on the nitrogen can be replaced by the usual blocking groups, such as, for example, by an acyl or silyl residue, such as the trialkylsilyl, especially the tert-butyldimethylsilyl group which, after termination of the reaction, are split off in accordance with the usual methods, e.g. by treatment with acids, such as dilute mineral acid, trifluoroacetic acid, or also inorganic bases, such as alkali hydroxide or fluorides, such as tetrabutylammonium fluoride at room temperature. The reaction is ended after about 5 minutes up to 2 hours; if desired, the mixture can be agitated for another 1-2 hours at room temperature. A protecting gas atmosphere is suitably utilized, such as argon or nitrogen.

The reaction with the ketone is carried out in the aforementioned aprotic solvents, such as ethers and hydrocarbons at low temperatures of 0° C. to −78° C., whereafter the reaction mixture is stirred at 0° C. to room temperature. Water is split off by using the usual methods, such as, for example, with the use of acids such as mineral acid, thionyl chloride/pyridine, or adding anhydrous copper sulfate.

Hydrogenation of double bonds is preferably conducted catalytically, for example with noble metal catalysts, such as platinum or palladium, optionally on suitable supports, such as carbon, in protic solvents such as alcohols, e.g. methanol, ethanol, and others, at room temperature up to the boiling temperature of the solvent, under normal pressure or under $H_2$ pressure.

Alkylation, arylation or acylation of an imino group take place according to known methods. For example, the imino compound is dissolved in a polar solvent and heated in the presence of a base with an alkyl, aryl or acyl halogenide to about 40°-50° C. Examples of suitable polar solvents are dimethylformamide, dimethylacetamide, cyclic ethers, such as tetrahydrofuran, dioxane, alcohols, such as ethanol, methanol, propanol, and suitable bases are, for example, sodium hydride, alkali alcoholates, such as sodium ethylate. Reaction with a haloaryl, for example iodobenzene, can also be conducted without solvents, preferably in the presence of pulverized copper.

Suitably, free hydroxy groups are blocked, prior to introducing the ring system, with the usual ether blocking groups, such as, for example, the tetrahydrofuranyl, tetrahydropyranyl residue; this residue can be split off, after termination of the reaction, in accordance with conventional methods, for example with acids. Acids suitable for the splitting off step are inorganic or organic acids, such as, for example, pyridinium tosylate, HCl, p-toluenesulfonic acid. The splitting off step is customarily performed in protic solvents, such as alcohols (methanol, ethanol or acetone) at room temperature up to the boiling temperature of the solvent.

The subsequent etherification can also take place according to conventional methods, such as, for example, by reaction with a corresponding tosylate or halogenide, such as chloride, bromide or iodide, in the presence of a base, such as pulverized KOH or tetrabutylammonium hydrogen sulfate. The etherification can be performed in protic solvents, such as alcohols, for example, methanol, ethanol, propanol or aprotic dipolar solvents, such as dimethylformamide, dimethyl sulfoxide, tetrahydrofuran, at room temperature up to the boiling temperature of the solvent.

Separation of isomers can be effected with known methods, such as, for example, crystallization, salt formation and chromatography.

The novel compounds of Formula I are pharmacologically active agents which are especially suitable as psychopharmaceuticals for mammalian, e.g., human medicine on account of their biological efficacy. Their mechanism of activity is based on reinforcement of neurotransmission beyond transmitter receptors on the basis of increase availability of cycloadenosine monophosphate due to intraneuronal phosphodiesterase inhibition affecting, in particular, affective and cognitive disturbances in neurodegenerative diseases of mammals, especially humans. Anticholinergic side effects, such as cardiovascular side effects or rise in intraocular pressure in case of glaucoma patients has not been observed. Consequently the compounds according to this invention are suitable for the treatment of presenile and senile dementia, analogously to, e.g., piracetam, Parkinson's disease analogously to L-DOPA or dopamine agonists, senile depression analogously to tricyclin, e.g., imipramine, and dementia due to alcohol abuse analogously to, e.g., piracetam.

The correlation between the neurotransmission reinforcing properties and effective and cognitive applications in humans can be established according to the methods described previously (Wachtel, H. and Schneider, H. H., Neuropharmacology 25: 1119–1126, 1986; and Randt, C. T. et al., Pharmacol. Biochem. Behav. 17: 667–680, 1982).

Based on their profile of effectiveness, compounds of general Formula I also exhibit peripheral effects and show anti-inflammatory, bronchospasmolytic, antiproliferative, thrombocyte-aggregation-inhibiting, and tocolytic properties.

They can be formulated into preparations, for example, for oral and parenteral administration.

Suitable formulating aids are physiologically compatible organic and inorganic excipients inert with respect to the compounds of this invention.

Examples of suitable excipients are water, saline solutions, alcohols, polyethylene glycols, polyhydroxyethoxylated castor oil, gelatin, lactose, amylose, magnesium stearate, talc, silicic acid, fatty acid mono- and -diglycerides, pentaerythritol fatty acid esters, hydroxymethylcellulose and polyvinylpyrrolidone.

The pharmaceutical preparations can be sterilized and/or combined with auxiliary agents, such as lubricants, preservatives, stabilizers, wetting agents, emulsifiers, buffers, and colorants.

Especially suited for parenteral use are injection solutions or suspensions, especially aqueous solutions of the active compounds in polyhydroxyethoxylated castor oil. Also suitable as the vehicle systems are auxiliary surfactants, such as salts of the bile acids or animal or vegetable phospholipids, but also mixtures thereof, as well as liposomes or their components.

Especially suitable for oral administration are tablets, dragees or capsules with talc and/or a hydrocarbon vehicle or binder, such as, for example, lactose, cornstarch, or potato starch. Administration can also take place in liquid form, such as, for example, as an elixir optionally combined with a sweetener.

The compounds according to this invention are introduced in a dosage unit of 0.0015–0.75 mg/kg of body weight of active compound in a physiologically acceptable excipient.

The compounds of this invention are utilized in a dose of 0.0015–0.75 mg/kg of body weight per day, preferably 0.015–0.15 mg/kg of body weight per day.

The starting compounds are known or can be prepared in accordance with methods known per se. Thus, 3-unsubstituted 4-alkoxyphenyl derivatives can be conventionally halogenated, for example, with elemental halogen or halogen acids, or the 3-OH-substituted phenyl derivative is conventionally trifluoromethanesulfonylated. The starting compounds are described, for example, in the patents set forth hereinabove.

The zinc, tin or boron organyls can, in part, be purchased or obtained, for example, in accordance with the method disclosed in Houben Weyl 13/6 (tin), 13/3a and 3b (boron), as well as J. Org. Chemie 42 : 1821 (1977) (zinc). The starting compounds and examples set forth below are to explain the process of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding German application P 38 23 299.5, are hereby incorporated by reference.

EXAMPLES

Example A 4-(4-Methoxy-3-trifluoromethanesulfonyloxyphenyl)-pyrrolidin-2-one Under exclusion of moisture and using a protective gas, 10.35 g (50 millimoles) of 4-(4-methoxy-3-hydroxyphenyl)pyrrolidin-2-one is introduced into 500 ml of methylene chloride. combined with 20 g of dimethylaminopyridine, and cooled to 0° C. Then a solution of 8.7 ml of trifluoromethanesulfonic acid anhydride in 100 ml of methylene chloride is gradually added dropwise and the mixture is stirred for ½ hour at 0° C. The reaction mixture is then combined with 300 ml of water and 200 ml of 1N hydrochloric acid and extracted. The methylene chloride phase is washed in succession with 300 ml of 1N hydrochloric acid and 300 ml of water, dried, filtered, and concentrated. Recrystallization of the residue from ethyl acetate/hexane yields 14.35 g (85% of theory). The product is 4-(4-methoxy-3-trifluoromethanesulfonyloxyphenyl)pyrrolidin-2-one, mp 99°–101° C.

Example B 4-(3-Iodo-4-methoxyphenyl)pyrrolidin-2-one

A solution of 19.1 g of 4-(4-methoxyphenyl)-pyrrolidin-2-one (100 mmol) in 200 ml of glacial acetic acid, 4.8 ml of water and 1.2 ml of concentrated sulfuric acid is combined with 3.44 g (19.55 mmol) of iodic acid and 8.64 g (70 mmol) of iodine and stirred at a bath temperature of 80° C. for 10 hours. Subsequently, the mixture is concentrated on a rotary evaporator up to onset of crystallization, cooled, the crystalline precipitate is suctioned off and recrystallized from ethyl acetate, thus obtaining 25.7 g (81% of theory) of 4-(3-iodo-4-methoxyphenyl)pyrrolidin-2-one, mp 158° C.

Example C 4-(3-Bromo-4-methoxyphenyl)pyrrolidin-2-one 190 mg (1 mmol) of 4-methoxyphenylpyrrolidin-2-one is dissolved in 1 ml of glacial acetic acid and combined dropwise at room temperature with 160 mg of bromine in 0.5 ml of glacial acetic acid. After one hour of agitation, the mixture is diluted with water. Suctioning off and drying yield 220 mg (81% of theory) of 4-(3-bromo-4-methoxyphenyl)pyrrolidin-2-one, mp 151°–154° C.

Example D 4-(3-Bromo-4-methoxyphenyl)-1-tert-butyldimethylsilylpyrrolidin-2-one Under nitrogen, 540 mg (2 mmol) of 4-(3-bromo-4-methoxyphenyl)pyrrolidin-2-one in 10 ml of dimethylformamide is combined with 60 mg (2 mmol) of sodium hydride. After 20 minutes of stirring, after cooling to 0° C., 300 mg (2 mmol) of tert-butyldimethylsilyl chloride in 5 ml of dimethylformamide is added dropwise and the mixture stirred at 0° C. for 30 minutes as well as at room temperature for 30 minutes. After concentration, the mixture is distributed in ethyl acetate/water. The ethyl acetate phase is dried, filtered and concentrated and the residue is chromatographed over silica gel with methylene chloride:ethanol=10:1 as the eluent, thus obtaining 420 mg of 4-(3-bromo-4-methoxyphenyl)-1-tert-butyldimethylsilylpyrrolidin-2-one, mp 150°–152° C.

Example 1

4-(2,3'-Dimethoxy-5-biphenylyl)pyrrolidin-2-one

A solution is prepared from 339 mg of 4-(4-methoxy-3-trifluoromethanesulfonyloxyphenyl)-pyrrolidin-2-one in 9 ml of toluene and 4 ml of ethanol and stirred for 5 minutes under argon at room temperature with 38 mg of tetrakis(triphenylphosphine) palladium(0). After addition of 172 mg of m-methoxyphenylboronic acid and 1.3 ml of 2-molar sodium carbonate solution, the mixture is heated to 90° C. for 4 hours. After adding ethyl acetate and water, the organic phase is separated, washed neutral with saturated sodium chloride solution, dried over sodium sulfate, and concentrated. Recrystallization from alcohol/ethyl acetate/petroleum ether (40°–60° C.) yields 187 mg of compound having a melting point of 137°–139° C.

The following compounds are produced analogously:

4-[2-methoxy-3'-(tetrahydropyran-2-yloxy)-5-biphenylyl]pyrrolidin-2-one as an oil, 4-(3',5'-dichloro-6-methoxy-3-biphenylyl)-pyrrolidin-2-one, mp 162°–164° C., 4-(2-methoxy-5-biphenylyl)pyrrolidin-2-one, mp 153°–154° C., 4-(2-methoxy-4'-methyl-5-biphenylyl)pyrrolidin-2-one, mp 146°–147° C., 4-(2,4'-dimethoxy-5-biphenylyl)pyrrolidin-2-one, mp 169° C., 4-[4-methoxy-3-(2-furyl)phenyl]pyrrolidin-2-one, mp 152°–153° C., 4-[4-methoxy-3-(2-thienyl)phenyl]pyrrolidin-2-one, mp 125° C., 4-[4-methoxy-3-(3-thienyl)phenyl]pyrrolidin-2-one, mp 135°–136° C., 4-(2',4'-dichloro-6-methoxy-3-biphenylyl)pyrrolidin-2-one, mp 145°–146° C., 4-(2,2'-dimethoxy-5-biphenylyl)pyrrolidin-2-one, mp 116°–117° C., 4-(4'-chloro-6-methoxy-3-biphenylyl)pyrrolidin-2-one, mp 162°–163° C., 4-(3'-chloro-2-methoxy-5-biphenylyl)pyrrolidin-2-one, mp 143°–144° C., 4-(2-methoxy-3'-methyl-5-biphenylyl)pyrrolidin-2-one, mp 159°–160° C.

Example 2

4-(3-Hydroxy-2-methoxy-5-biphenylyl)pyrrolidin-2-one

A solution is prepared from 894 mg of 4-[2-methoxy-3'-(tetrahydropyran-2-yloxy)-5-biphenylyl]-2-pyrrolidin-2-one in 10 ml of ethanol and 2 ml of water and the solution is heated under reflux for one hour with 754 mg of pyridinium p-toluenesulfonate. After removal of the solvent by distillation, the reaction product is taken up in ethyl acetate and the solution washed in succession with saturated sodium bicarbonate solution as well as with saturated sodium chloride solution, dried over sodium sulfate, filtered, and concentrated. After column chromatography over 150 g of silica gel (40–63 μm) with methylene chloride/ethanol 10:1 as the eluent, 464 mg of 4-(3'-hydroxy-2-methoxy-5-biphenylyl)pyrrolidin-2-one is isolated as an oil.

Example 3

4-(3'-Cyclopentyloxy-2-methoxy-5-biphenylyl)pyrrolidin-2-one 100 mg of 4-(3'-hydroxy-2-methoxy-5-biphenylyl)-2-pyrrolidin-2-one and 90 microliters of cyclopentyl bromide are heated under reflux for 3 hours in 10 ml of absolute ethanol with 70 mg of potassium hydroxide powder. After concentration of the mixture, the latter is taken up in ethyl acetate, washed with saturated sodium chloride solution, dried over sodium sulfate, filtered, and concentrated. From the residue, column chromatography on 75 g of silica gel (40–63 μm) with methylene chloride/ethanol 10:1 as the eluent yields 79 mg of 4-(3'-cyclopentyloxy-2-methoxy-5-biphenylyl)-pyrrolidin-2-one as a foam.

Example 4

Mixture of 4-(3-(cyclopent-1-en-1-yl)-4-methoxyphenyl]-pyrrolidin-2-one and 4-[3-(cyclopent-2-en-1-yl)-4-methoxyphenyl]pyrrolidin-2-one In a pressurized reactor, 4.7 g (14.8 mmol) of 4-(3-iodo-4-methoxyphenyl)pyrrolidin-2-one is dissolved in 100 ml of dimethylformamide and combined with 2.56 ml of triethylamine, 400 mg of tri-ortho-tolylphosphine, 170 mg of palladium acetate and 2.5 ml (28 mmol) of cyclopentene (28 mmol). The reaction solution is allowed to react under argon in the sealed pressure vessel at a temperature of 120°–125° C. for 24 hours. Then the mixture is evaporated, taken up in ethyl acetate and washed with saturated sodium chloride solution, dried over "Sikkon" (anhydrous calcium sulfate), filtered, and concentrated by evaporation. The residue of 4.4 g of a brown oil is chromatographed over silica gel with methylene chloride:ethanol=1:1 as the eluent, yielding 3 g (79% of theory) of the above-mentioned mixture as an oil.

The following compounds are produced analogously:
mixture of 4-[3-(cyclohex-1-en-1-yl)-4-methoxyphenyl]-pyrrolidin-2-one and 4-[3-(cyclohex-2-en-1-yl)-4-methoxypenyl]pyrrolidin-2-one, mp 138° C.,
mixture of 4-[3-(cyclohept-1-en-1-yl)-4-methoxyphenyl]-pyrrolidin-2-one and 4-[3-(cyclohept-2-en-1-yl)-4-methoxyphenyl]pyrrolidin-2-one as an oil,
4-[3-(inden-2-yl)-4-methoxyphenyl]-2-pyrrolidin-2-one, mp 163°–165° C.

Example 5

4-(3-Cyclopentyl-4-methoxyphenyl)pyrrolidin-2-one 3.6 g (14 mmol) of the isomer mixture (Example 4) is hydrogenated in 100 ml of ethanol with 250 mg of platinum dioxide under normal conditions. Then the product is filtered off from the catalyst and the filtrate is evaporated. Recrystallization of the residue from ethyl acetate yields 2.3 g (63% of theory) of 4-(3-cyclopentyl-4-methoxyphenyl)pyrrolidin-2-one, mp 139° C.

The following compounds are produced analogously:
4-(3-cyclohexyl-4-methoxyphenyl)pyrrolidin-2-one, mp 164° C.,
4-(3-cycloheptyl-4-methoxyphenyl)pyrrolidin-2-one, mp 157° C.,
4-[3-(indanyl)-4-methoxyphenyl]-2-pyrrolidone, mp 157° C.,
4-[3-(exo-norborn-2-yl)-4-methoxyphenyl]-2-pyrrolidone, mp 149°–151° C.

Example 6

4-[4-Methoxy-3-(1-hydroxycyclopent-1-yl)phenyl]-pyrrolidin-2-one 2.2 g (0.7 mmol) of 4-(3-bromo-4-methoxy-phenyl)-1-tert-butyldimethylsilylpyrrolidin-2-one in 30 ml of absolute tetrahydrofuran is combined at −70° C. with 8.2 ml (0.7 ml) of a butyllithium solution in hexane. The mixture is allowed to warm up to 0° C., agitated at this temperature for 10 minutes, and again cooled to −70° C. Then a solution of 0.48 g of cyclopentanone in 10 ml of tetrahydrofuran is added dropwise thereto, the mixture is allowed to warm gradually to 0° C., and stirred at this temperature for one hour. After addition of 0.1 ml of water, the mixture is evaporated and chromatographed over silica gel with methylene chloride:acetone=1:1 as the eluent. After repeating chromatography of the corresponding fractions over silica gel with methylene chloride:ethanol=10:1 as the eluent, 110 mg of 4-[4-methoxy-3-(1-hydroxycyclopent-1-yl)phenyl]pyrrolidin-2-one is obtained as an oil.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of the formula I

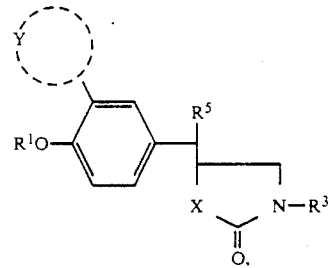

wherein
$R^1$ is $C_{1-4}$-alkyl,
$R^3$ is hydrogen, $C_{1-4}$-alkyl, acyl, or $C_{6-12}$-aryl,
$R^5$ is hydrogen or $C_{1-4}$-alkyl,
X is $CH_2$, and
Y is phenyl, biphenylyl, indenyl, naphthyl, thienyl, furyl, tetrahydrofuranyl, pyranyl, tetrahydropyranyl, pyrrolyl, pyrrolidinyl, benzo[1]thienyl, benzofuryl, cycloalkyl, cycloalkenyl, phenylcycloalkyl, bicycloalkyl, bicycloalkenyl, a stereoisomer of a compound of Formula I or a mixture of stereoisomers thereof.

2. A compound according to claim 1, wherein $R^1 = CH_3$.

3. A compound according to claim 1, wherein $R^3 = H$.

4. 4-(2,3'-dimethoxy-5-biphenylyl)pyrrolidin-2-one, 4-(3',5'-dichloro-6-methoxy-3-biphenylyl)pyrrolidin-2-one, 4-(2-methoxy-5-biphenylyl)pyrrolidin-2-one, 4-

(2-methoxy-4'-methyl-5-biphenylyl)pyrrolidin-2-one, 4-(2,4'-dimethoxy-5-biphenylyl)pyrrolidin-2-one, 4-[4-methoxy-3-(2-furyl)phenyl]pyrrolidin-2-one, 4-[4-methoxy-3-(2-thienyl)phenyl]pyrrolidin-2-one, 4-[4-methoxy-3-(3-thienyl)phenyl]pyrrolidin-2-one, 4-(2',4'-dichloro-6-methoxy-3-biphenylyl)pyrrolidin-2-one, 4-(2,2'-dimethoxy-5-biphenylyl)pyrrolidin-2-one, 4-(4'-chloro-6-methoxy-3-biphenylyl)pyrrolidin-2-one, 4-(3'-chloro-2-methoxy-5-biphenylyl)pyrrolidin-2-one, 4-(2-methoxy-3'-methyl-5-biphenylyl)pyrrolidin-2-one, 4-(3'-cyclopentyloxy-2-methoxy-5-biphenylyl)pyrrolidin-2-one, 4-(3-cyclopentyl-4-methoxyphenyl)pyrrolidin-2-one, 4-(3-cyclohexyl-4-methoxyphenyl)pyrrolidin-2-one, or 4-(3-cycloheptyl-4-methoxyphenyl)pyrrolidin-2-one, each a compound of claim 1.

5. A compound according to claim 1, wherein Y is cyclopropyl, cyclobutyl, cyclopentyl, cyclohexyl, cycloheptyl, cyclooctyl, cyclohexenyl, cyclopentenyl, cycloheptenyl, bicycloheptyl, bicycloheptenyl or indan-2-yl.

6. A compound according to claim 1, wherein Y is pyrrolidinyl, tetrahydrofuranyl, or tetrahydropyranyl.

7. A compound according to claim 1, wherein Y is $C_{3-7}$-cycloalkyl, $C_{3-7}$-cycloalkenyl, norbornane, 1-hydroxy $C_{3-7}$-cycloalkyl, or phenylcycloalkyl.

8. A compound according to claim 1, wherein $R^3$ is phenyl.

9. A compound according to claim 1, wherein $R^3$ is $C_{1-4}$-alkanoyl.

10. A compound according to claim 1, wherein $R^1$ is $CH_3$ and $R^3$ is H.

11. A pharmaceutical composition comprising a compound of claim 1 and a pharmaceutically acceptable carrier.

12. A pharmaceutical composition comprising a compound of claim 10 and a pharmaceutically acceptable carrier.

13. A method for the inhibition of cycloadenosine monophosphate degradation by phosphodiesterase in mammals, comprising administering an effective amount of a compound of claim 1.

14. A method for the production of an anti-inflammatory, bronchospasmolytic, anti-proliferative, thrombocyte-aggregation-inhibiting or tocolytic effect in a mammal comprising administering an effective amount of a compound of claim 1.

15. A method of treating presenile or senile dementia, Parkinson's disease, senile depression or alcohol-induced dementia comprising administering an effective amount of a compound of claim 1.

16. A method for the treatment of a neurodegenerative disease, comprising administering an effective amount of a compound of claim 1.

17. 4-(3'-chloro-2-methoxy-5-biphenyl)pyrrolidin-2-one, a compound of claim 1.

18. A compound of claim 1, wherein Y is (a) phenyl optionally mono- or disubstituted with halogen, alkyl, $NH_2$, or $OR^2$, and $R^2$ is H, $C_{1-4}$-alkyl, $C_{3-7}$-cycloalkyl, tetrahydrofuranyl, or tetrahydropyranyl, or (b) thienyl.

19. A compound of claim 1, wherein Y is phenyl, furyl, thienyl, cyclopentenyl, indenyl, cyclohexenyl, cycloheptenyl, cyclopentyl, cyclohexyl, cycloheptyl, indanyl, norbornyl, or 1-hydroxycyclopentyl.

* * * * *

UNITED STATES PATENT AND TRADEMARK OFFICE
CERTIFICATE OF CORRECTION

PATENT NO. : 5,064,854          Page 1 of 2
DATED      : November 12, 1991
INVENTOR(S): Andreas HUTH et al.

It is certified that error appears in the above-indentified patent and that said Letters Patent is hereby corrected as shown below:

Replace formula I in the Abstract, column 1 and claim 1 with the correct structure as shown below:

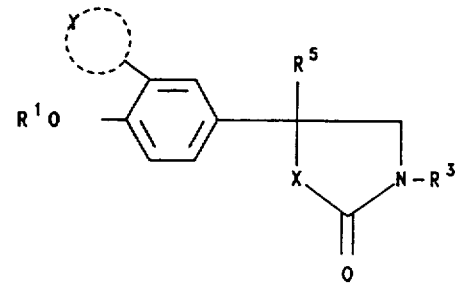

Replace formula II (column 3, lines 32-41) in the same manner:

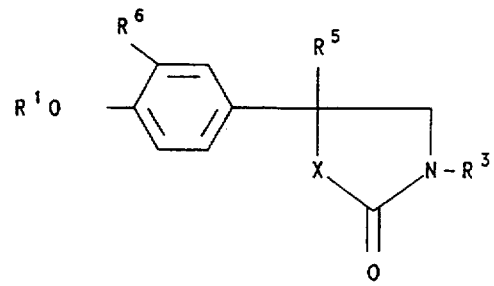

UNITED STATES PATENT AND TRADEMARK OFFICE
CERTIFICATE OF CORRECTION

PATENT NO. : 5,064,854

DATED : November 12, 1991

INVENTOR(S) : Andreas HUTH et al.

It is certified that error appears in the above-indentified patent and that said Letters Patent is hereby corrected as shown below:

Column 8,

The title in Example 2:

Should read:

4-(3'-Hydroxy-2-methoxy-5-biphenylyl-pyrrolidin-2-one)

Signed and Sealed this

Seventh Day of January, 1997

Attest:

BRUCE LEHMAN

*Attesting Officer*   *Commissioner of Patents and Trademarks*